(12) United States Patent
Sanford

(10) Patent No.: US 9,615,929 B2
(45) Date of Patent: Apr. 11, 2017

(54) POSTERIOR-STABILIZED TOTAL KNEE PROSTHESIS

(75) Inventor: Adam H. Sanford, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 285 days.

(21) Appl. No.: 12/692,371

(22) Filed: Jan. 22, 2010

(65) Prior Publication Data

US 2010/0249940 A1 Sep. 30, 2010

Related U.S. Application Data

(60) Provisional application No. 61/146,745, filed on Jan. 23, 2009.

(51) Int. Cl.
*A61F 2/38* (2006.01)
*A61F 2/30* (2006.01)

(52) U.S. Cl.
CPC .. *A61F 2/3886* (2013.01); *A61F 2002/30199* (2013.01); *A61F 2230/0063* (2013.01)

(58) Field of Classification Search
CPC .......... A61F 2002/30604; A61F 2/3859; A61F 2220/0033; A61F 2220/0025; A61F 2/38; A61F 2/389; A61F 2/36
USPC .......................................... 623/20.14–20.36
See application file for complete search history.

(56) References Cited

U.S. PATENT DOCUMENTS

| | | |
|---|---|---|
| 3,798,679 A | 3/1974 | Ewald |
| 3,816,855 A | 6/1974 | Saleh |
| 4,112,522 A | 9/1978 | Dadurian et al. |
| 4,209,861 A * | 7/1980 | Walker et al. ............. 623/20.27 |
| 4,215,439 A * | 8/1980 | Gold ..................... A61F 2/3886 |
| | | 623/20.26 |
| 5,147,405 A | 9/1992 | Van Zile |
| 5,219,362 A | 6/1993 | Tuke et al. |
| 5,282,870 A | 2/1994 | Moser et al. |
| 5,330,534 A * | 7/1994 | Herrington et al. ....... 623/20.27 |
| 5,358,527 A | 10/1994 | Forte |

(Continued)

FOREIGN PATENT DOCUMENTS

| | | |
|---|---|---|
| EP | 0123016A1 A1 | 10/1984 |
| EP | 1121074 B1 | 7/2008 |

(Continued)

OTHER PUBLICATIONS

Written Opinion and International Search Report mailed Apr. 20, 2010 in related International Application No. PCT/US2010/021818.

(Continued)

*Primary Examiner* — Ann Schillinger
(74) *Attorney, Agent, or Firm* — Schwegman Lundberg & Woessner, P.A.

(57) ABSTRACT

In an orthopaedic knee joint prosthesis, an intercondylar fossa of a femoral component cooperates with a spine formed in a tibial component to reproduce the screw home mechanism of a natural knee. When the femoral component and tibial component are positioned to correspond with slight flexion of the knee, the components are mutually rotationally locked against internal or external rotation. At higher degrees of flexion, such as greater than about 10-20 degrees of flexion, internal/external rotation of the tibia is permitted. The tibia is in an externally rotated position when locked, thereby reproducing the screw home mechanism and providing high stability.

15 Claims, 6 Drawing Sheets

(56) References Cited

U.S. PATENT DOCUMENTS

| | | | |
|---|---|---|---|
| 5,370,699 A * | 12/1994 | Hood et al. ................. | 623/20.28 |
| 5,413,604 A | 5/1995 | Hodge | |
| 5,549,686 A | 8/1996 | Johnson et al. | |
| 5,728,162 A | 3/1998 | Eckhoff | |
| 6,013,103 A | 1/2000 | Kaufman et al. | |
| 6,056,779 A | 5/2000 | Noyer et al. | |
| 6,342,075 B1 | 1/2002 | MacArthur | |
| 6,406,497 B2 | 6/2002 | Takei | |
| 6,475,241 B2 | 11/2002 | Pappas | |
| 6,491,726 B2 | 12/2002 | Pappas | |
| 6,558,426 B1 | 5/2003 | Masini | |
| 6,660,039 B1 * | 12/2003 | Pothier ................. | A61F 2/3886 623/20.29 |
| 6,699,291 B1 | 3/2004 | Augoyard et al. | |
| 6,764,516 B2 | 7/2004 | Pappas | |
| 6,783,550 B2 | 8/2004 | MacArthur | |
| 6,797,005 B2 | 9/2004 | Pappas | |
| 7,081,137 B1 | 7/2006 | Servidio | |
| 7,160,330 B2 | 1/2007 | Axelson, Jr. et al. | |
| 7,309,362 B2 | 12/2007 | Yasuda et al. | |
| 7,326,252 B2 | 2/2008 | Otto et al. | |
| 7,351,263 B2 | 4/2008 | Afriat | |
| 7,413,577 B1 | 8/2008 | Servidio | |
| 7,615,054 B1 | 11/2009 | Bonutti | |
| 7,635,390 B1 | 12/2009 | Bonutti | |
| 8,192,498 B2 | 6/2012 | Wagner et al. | |
| 8,236,061 B2 | 8/2012 | Heldreth et al. | |
| 8,491,661 B2 | 7/2013 | Mouillet et al. | |
| 8,932,365 B2 | 1/2015 | Parisi et al. | |
| 9,132,014 B2 | 9/2015 | Sanford et al. | |
| 2003/0009232 A1 | 1/2003 | Metzger et al. | |
| 2004/0143339 A1 * | 7/2004 | Axelson, Jr. .......... | A61F 2/3886 623/20.21 |
| 2005/0209701 A1 | 9/2005 | Suguro et al. | |
| 2007/0135925 A1 | 6/2007 | Walker | |
| 2007/0135926 A1 | 6/2007 | Walker | |
| 2007/0173946 A1 | 7/2007 | Bonutti | |
| 2007/0233269 A1 | 10/2007 | Steines et al. | |
| 2008/0097615 A1 | 4/2008 | Lipman et al. | |
| 2008/0119940 A1 | 5/2008 | Otto et al. | |
| 2009/0210066 A1 | 8/2009 | Jasty | |
| 2009/0222103 A1 | 9/2009 | Fitz et al. | |
| 2009/0306786 A1 | 12/2009 | Samuelson | |
| 2009/0319047 A1 | 12/2009 | Walker | |
| 2009/0319049 A1 | 12/2009 | Shah et al. | |
| 2009/0326665 A1 | 12/2009 | Wyss et al. | |
| 2010/0016977 A1 | 1/2010 | Masini | |
| 2010/0016979 A1 | 1/2010 | Wyss et al. | |
| 2010/0036499 A1 | 2/2010 | Pinskerova | |
| 2010/0042224 A1 | 2/2010 | Otto et al. | |
| 2010/0161067 A1 | 6/2010 | Saleh et al. | |
| 2010/0305708 A1 | 12/2010 | Lang | |
| 2010/0329530 A1 | 12/2010 | Lang et al. | |
| 2011/0144760 A1 | 6/2011 | Wong et al. | |
| 2012/0089234 A1 | 4/2012 | Mouillet et al. | |
| 2012/0095563 A1 | 4/2012 | Sanford et al. | |
| 2012/0095564 A1 | 4/2012 | Mihalko et al. | |
| 2012/0179265 A1 | 7/2012 | Wyss et al. | |
| 2012/0323337 A1 | 12/2012 | Parisi et al. | |
| 2013/0006373 A1 | 1/2013 | Wyss et al. | |
| 2013/0190884 A1 | 7/2013 | Hashida | |
| 2013/0197653 A1 | 8/2013 | Hawkins et al. | |
| 2013/0204380 A1 | 8/2013 | Mouillet et al. | |
| 2014/0243989 A1 | 8/2014 | Nabeshima et al. | |
| 2015/0025644 A1 | 1/2015 | Heggendorn et al. | |
| 2015/0134067 A1 | 5/2015 | Qu et al. | |
| 2015/0164646 A1 | 6/2015 | Muratoglu | |
| 2015/0305873 A1 | 10/2015 | Sanford et al. | |

FOREIGN PATENT DOCUMENTS

| | | |
|---|---|---|
| EP | 1555962 B1 | 2/2011 |
| EP | 2324799 A2 | 5/2011 |
| EP | 2335654 A1 | 6/2011 |
| JP | 2004-166802 | 6/2004 |
| WO | WO-0023011 A1 | 4/2000 |
| WO | WO-2005051240 A1 | 6/2005 |
| WO | WO-2006058057 A2 | 6/2006 |
| WO | WO-2007109641 A2 | 9/2007 |
| WO | WO-2011018441 A1 | 2/2011 |
| WO | WO-2011072235 A2 | 6/2011 |
| WO | WO-2012112698 A2 | 8/2012 |
| WO | WO-2013007747 A1 | 1/2013 |

OTHER PUBLICATIONS

International Preliminary Report on Patentability mailed Aug. 4, 2011 from WIPO in related International Application No. PCT/US2010/021818.

Zimmer LPS Flex Fixed Bearing Knee Surgical Technique, Zimmer, Inc. 2004, 2007.

"U.S. Appl. No. 13/086,104, Final Office Action mailed Apr. 9, 2013", 8 pgs.

"U.S. Appl. No. 13/086,104, Non Final Office Action mailed Oct. 18, 2012", 12 pgs.

"U.S. Appl. No. 13/086,104, Response filed Feb. 19, 2013 to Non Final Office Action mailed Oct. 18, 2012", 16 pgs.

"U.S. Appl. No. 13/086,104, Response filed Jul. 9, 2013 to Final Office Action mailed Apr. 9, 2013", 13 pgs.

"U.S. Appl. No. 13/086,104, Response filed Oct. 1, 2012 to Restriction Requirement mailed Aug. 29, 2012", 6 pgs.

"U.S. Appl. No. 13/086,104, Restriction Requirement Received", 6 pgs.

"Bi-Cruciate Stabilized Knee System", Design Rationale, Smith & Nephew Journal, (2006), 20 pgs.

"Complete Knee Solution Surgical Technique for the CR-Flex Fixed Bearing Knee", Zimmer Nexgen, (2003), 22 pgs.

Li, Guoan, et al., "Anterior Cruciate Ligament Deficiency Alters the In Vivo Motion of the Tibiofemoral Cartilage Contact Points in Both the Anteroposterior and Mediolateral Directions", The Journal of Bone & Joint Surgery, (2006), 1826-1834.

"International Application Serial No. PCT/EP2012/063575, International Preliminary Report on Patentability mailed Dec. 2, 2013", 9 pgs.

"International Application Serial No. PCT/EP2012/063575, Written Opinion mailed", 7 pgs.

"U.S. Appl. No. 13/086,104, Advisory Action mailed Apr. 1, 2015", 3 pgs.

"U.S. Appl. No. 13/086,104, Final Office Action mailed Jan. 27, 2015", 12 pgs.

"U.S. Appl. No. 13/086,104, Non Final Office Action mailed May 28, 2014", 15 pgs.

"U.S. Appl. No. 13/086,104, Notice of Allowance mailed May 1, 2015", 5 pgs.

"U.S. Appl. No. 13/086,104, Response filed Mar. 26, 2015 to Final Office Action mailed Jan. 27, 2015", 16 pgs.

"U.S. Appl. No. 13/086,104, Response filed Apr. 21, 2015 to Advisory Action mailed Apr. 1, 2015", 16 pgs.

"U.S. Appl. No. 13/086,104, Response filed Nov. 24, 2014 to Non Final Office Action mailed May 28, 2014", 15 pgs.

"U.S. Appl. No. 14/131,986, Preliminary Amendment filed Jan. 10, 2014", 3 pgs.

"U.S. Appl. No. 14/509,753, Preliminary Amendment filed Oct. 8, 2014", 3 pgs.

"International Application Serial No. PCT/EP2012/063575, Demand and Letter filed May 13, 2013", 11 pgs.

"International Application Serial No. PCT/EP2012/063575, International Search Report mailed Oct. 11, 2012", 5 pgs.

"U.S. Appl. No. 14/793,152, Preliminary Amendment filed Jul. 7, 2015", 3 pgs.

"U.S. Appl. No. 14/793,152, Supplemental Preliminary Amendment filed Jul. 9, 2015", 8 pgs.

"U.S. Appl. No. 14/509,753, Final Office Action mailed Jul. 7, 2016", 5 pgs.

"U.S. Appl. No. 14/509,753, Non Final Office Action mailed Jan. 25, 2016", 9 pgs.

(56) References Cited

OTHER PUBLICATIONS

"U.S. Appl. No. 14/509,753, Response filed May 4, 2016 to Non Final Office Action mailed Jan. 25, 2016", 14 pgs.

* cited by examiner

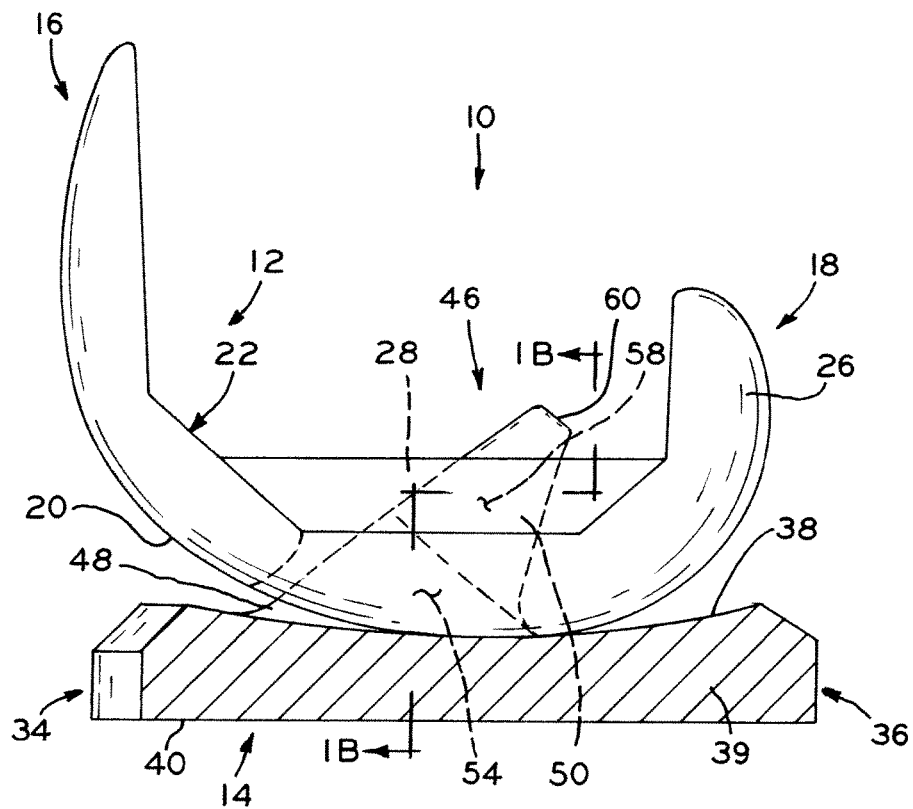
FIG_1A
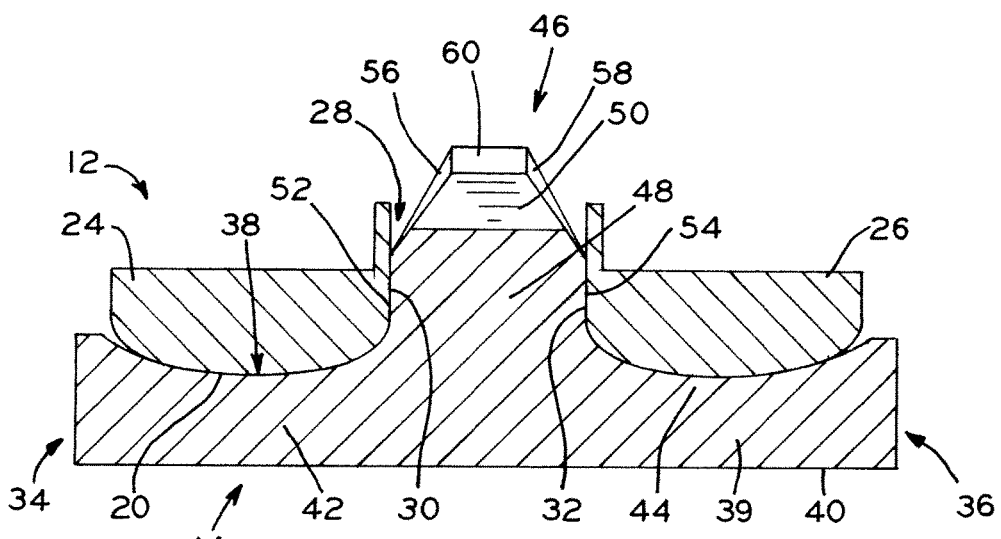
FIG_1B

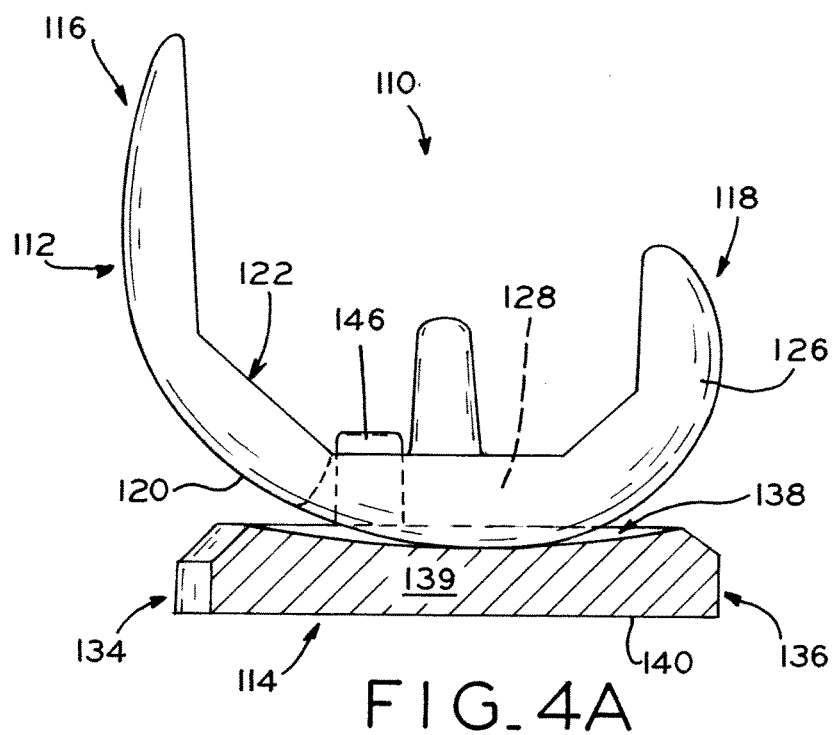
FIG_4A
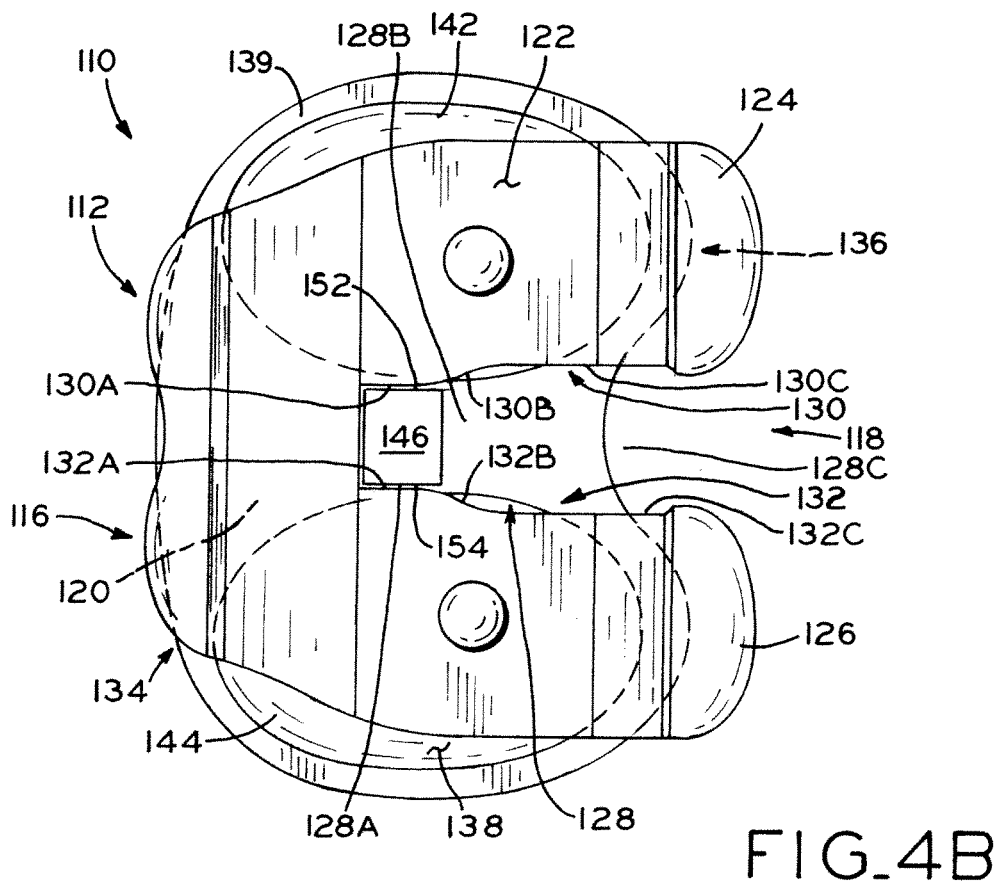
FIG_4B

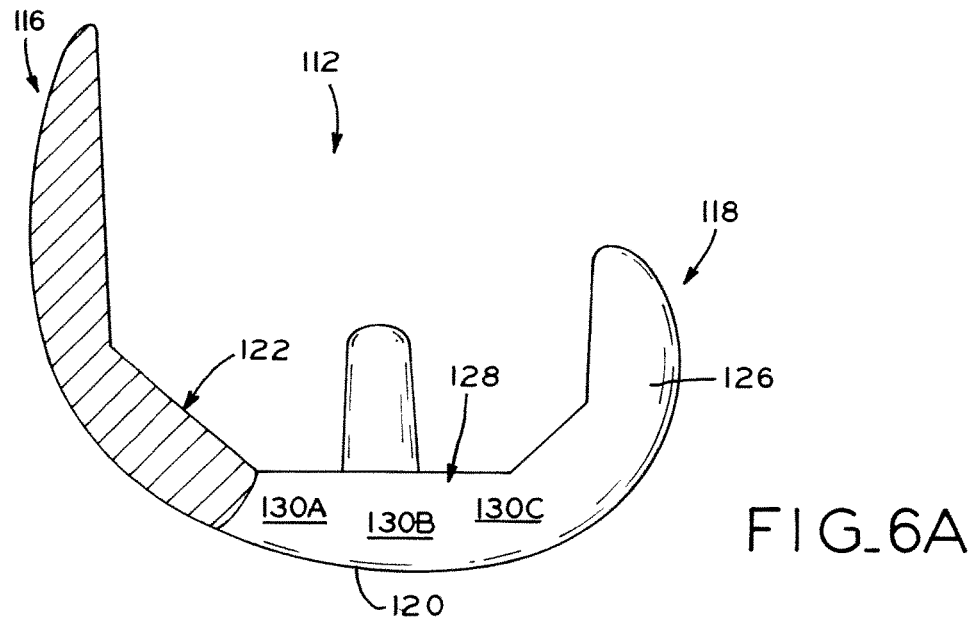
FIG_6A
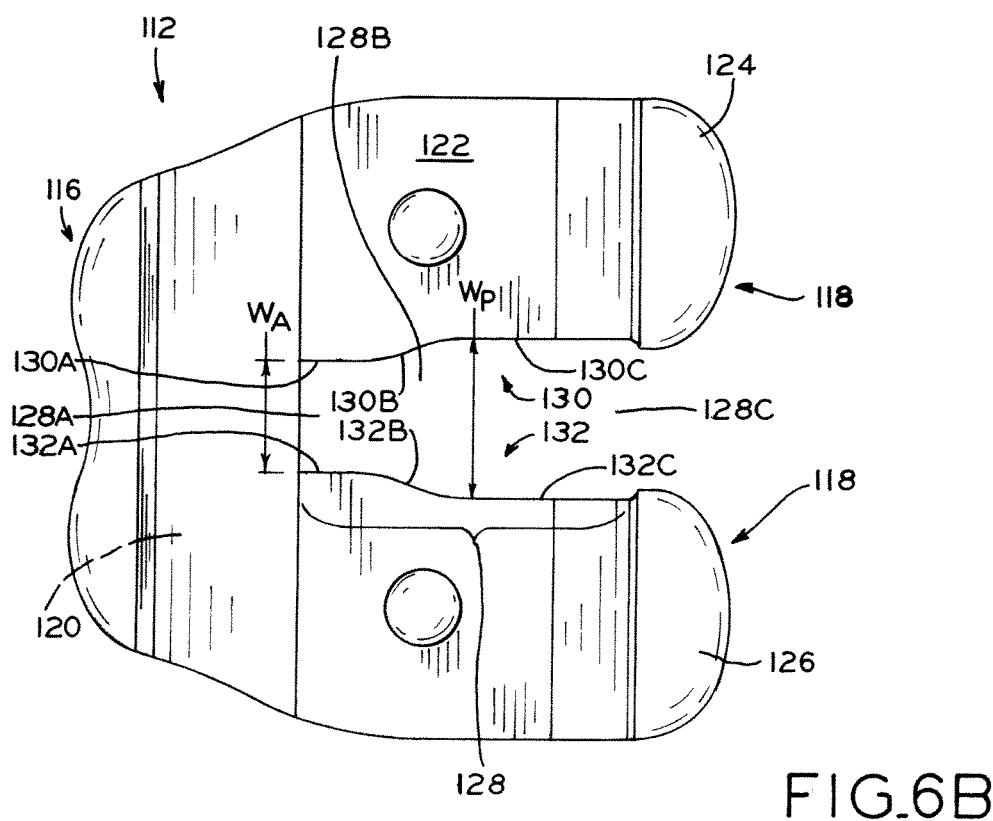
FIG.6B

POSTERIOR-STABILIZED TOTAL KNEE PROSTHESIS

CROSS REFERENCE TO RELATED APPLICATION

This application claims the benefit under Title 35, U.S.C. §119(e) of U.S. Provisional Patent Application Ser. No. 61/146,745, entitled POSTERIOR-STABILIZED TOTAL KNEE PROSTHESIS, filed on Jan. 23, 2009, the entire disclosure of which is expressly incorporated herein by reference.

BACKGROUND

1. Technical Field

The present invention relates to orthopedic prostheses and, specifically, to knee prostheses.

2. Description of the Related Art

Orthopedic prostheses are commonly utilized to repair and/or replace damaged bone and tissue in the human body. For example, a knee prosthesis may include a tibial component and/or a femoral component that replace damaged and/or destroyed bone in the tibia and/or femur and promote articulation similar to the natural, anatomical articulation of the knee joint.

In a natural knee, internal rotation of the tibia occurs when the knee is flexed from full extension (i.e., zero degrees flexion) to about 20 degrees flexion, and, conversely, external rotation of the tibia occurs when the knee is extended from about 20 degrees to full extension. This internal/external rotation is known as the "screw home" mechanism. The screw home mechanism is driven in part by the difference in the radii of curvature of the medial and lateral condyles of the distal femur. The externally rotated orientation of the anatomic tibia in full extension results in tightening of cruciate ligaments and "locks" the knee against internal/external rotation at the tibia-femur interface. The screw home mechanism thereby promotes stability of the tibia with respect to the femur when the knee is extended or slightly flexed.

In the final stages of knee extension, the tibia rolls anteriorly and the posterior cruciate ligament (PCL) elongates, causing translation of the femur relative to the tibia at the tibia-femur interface. The lateral side of the distal femoral articular surface experiences a relatively larger anterior translation as compared with the medial side of same. This anterior movement of the lateral distal femoral articular surface occurs during the last 20 degrees of knee extension results in external rotation of the tibia, and forms the basis for the screw home mechanism. Once in the extended position, internal/external rotation of the tibia is substantially prevented.

When the natural knee begins to flex from a position of full extension, the lateral side of the distal femoral articular surface translates posteriorly, elongating the anterior cruciate ligament (ACL). The lateral femoral articular surface experiences a relatively larger posterior translation as compared with the medial side of same. This posterior movement of the lateral distal femoral articular surface occurs during the first 20 degrees of knee flexion, and reverses the screw home mechanism. Once the knee is sufficiently flexed, such as about 20 degrees, internal/external rotation of the tibia is once again permitted.

SUMMARY

The present disclosure provides an orthopaedic knee joint prosthesis in which an intercondylar fossa of a femoral component cooperates with a spine formed in a tibial component to reproduce the screw home mechanism of a natural knee. When the femoral component and tibial component are positioned to correspond with slight flexion of the knee, the components are mutually rotationally locked against internal or external rotation. At higher degrees of flexion, such as greater than about 10-20 degrees of flexion, internal/external rotation of the tibia is permitted. As the knee joint prosthesis transitions from a flexion orientation to an extension orientation, the spine may interact with the intercondylar fossa to drive internal or external rotation of the knee, subsequently locking the tibia in the resulting rotated position.

In one embodiment, for example, a base portion of the tibial spine has a width corresponding with a width between the inner faces of the lateral and medial condyles of the femoral component (i.e., the intercondylar fossa). A peak portion of the tibial spine has a reduced width which is less than the width of the intercondylar fossa. When the femoral component and tibial spine are oriented in an extension orientation, the side walls of the intercondylar fossa closely engage the base of the spine to lock the tibia against internal/external rotation. When the tibial component and femoral component are in an extension orientation, such as at least 10 degrees of flexion, the side walls of the intercondylar fossa move so that they are adjacent the peak portion of the spine, thereby creating a space between the spine and the sidewalls of the intercondylar fossa that allows internal/external rotation.

In an alternative embodiment, the side walls of the intercondylar fossa of the femoral component may define a varying width along different anteroposterior locations. For example, the intercondylar fossa may define a narrow width at an anterior position, which closely conforms to the tibial spine to lock the tibia against external/internal rotation when the prosthesis is in an extension orientation. As the femoral component articulates with the tibial component during flexion, the intercondylar fossa grows wider to provide a space between the side walls of the intercondylar fossa and the tibial spine, thereby creating a space that permits internal/external rotation in larger amounts at larger degrees of flexion.

In one form thereof, the present invention provides a knee joint prosthesis moveable between an extension orientation and a flexion orientation, the prosthesis including a femoral component and a tibial component. The femoral component includes a lateral condyle having a lateral condylar inner wall, a medial condyle having a medial condylar inner wall, and an intercondylar fossa bounded on two sides by the lateral condylar inner wall and the medial condylar inner wall. The tibial component includes a tibial articulating surface, and a spine extending proximally from the tibial articulating surface. The spine includes a base adjacent the tibial articulating surface, and the base has a lateral base wall and an opposed medial base wall. A base width is defined between the lateral base wall and medial base wall. The spine includes a peak disposed proximally of the base, the peak having a lateral peak surface and an opposed medial peak surface, with a peak width defined between the lateral peak surface and medial peak surface. The peak width is less than the base width. The lateral condylar inner wall cooperates with the lateral base wall, and the medial condylar inner wall cooperates with the medial base wall to prevent internal rotation and external rotation of the tibial component when the knee joint prosthesis is in the extension orientation. The lateral condylar inner wall cooperates with the lateral peak surface, and the medial condylar inner wall cooperates with the medial peak surface to permit at least one of internal rotation and external rotation of the tibial component when the knee joint prosthesis is in the flexion orientation.

In another form thereof, the present invention provides a knee joint prosthesis moveable between an extension orientation and a flexion orientation, the prosthesis including a femoral component and a tibial component. The femoral component includes a lateral condyle having a lateral condylar inner wall defining an anterior lateral wall segment and a posterior lateral wall segment, a medial condyle having a medial condylar inner wall defining an anterior medial wall segment and a posterior medial wall segment, and an intercondylar fossa bounded on two sides by the lateral condylar inner wall and the medial condylar inner wall. The intercondylar fossa includes an anterior space between the anterior lateral wall segment and the anterior medial wall segment, and the intercondylar fossa includes a posterior space between the posterior lateral wall segment and the posterior medial wall segment. The tibial component includes an articulating surface and a spine extending proximally from the tibial articulating surface, the spine having a lateral spine wall and an opposed medial spine wall. The anterior space of the intercondylar fossa cooperates with the lateral spine wall and the medial spine wall to prevent internal rotation and external rotation of the tibial component when the knee joint prosthesis is in the extension orientation. The posterior space of the intercondylar fossa cooperates with at least one of the lateral spine wall and the medial spine wall to permit internal rotation and external rotation of the tibial component when the knee joint prosthesis is in the flexion orientation.

In yet another form thereof, the present invention provides a knee joint prosthesis moveable between an extension orientation and a flexion orientation, the prosthesis including a tibial component and a femoral component. The tibial component includes tibial means for guiding internal and external rotation of the tibial component, and the femoral component includes a femoral means for guiding internal and external rotation of the tibial component. The femoral means for guiding cooperates with the tibial means for guiding to prevent internal rotation and external rotation of the tibial component when the knee joint prosthesis is in the extension orientation. The femoral means for guiding cooperates with the tibial means for guiding to permit at least one of internal rotation and external rotation of the tibial component when the knee joint prosthesis is in the flexion orientation.

BRIEF DESCRIPTION OF THE DRAWINGS

The above mentioned and other features and advantages of this disclosure, and the manner of attaining them, will become more apparent and the invention itself will be better understood by reference to the following description of embodiments of the invention taken in conjunction with the accompanying drawings, where:

FIG. 1A is an elevation, partial section view of a knee joint prosthesis in accordance with the present disclosure, shown in an extension orientation;

FIG. 1B is an elevation, section, partial end view of the knee joint prosthesis shown in FIG. 1A, illustrating a multi-width spine;

FIG. 4A is an elevation, section, plan view of a knee joint prosthesis in accordance with the present disclosure, shown in an extension orientation;

FIG. 4B is a plan view of the knee joint prosthesis shown in FIG. 4A;

FIG. 6A is an elevation, section view of a femoral component of the knee joint prosthesis of FIG. 4A; and FIG. 6B is a plan view of the femoral component of FIG. 3B;

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 2A:
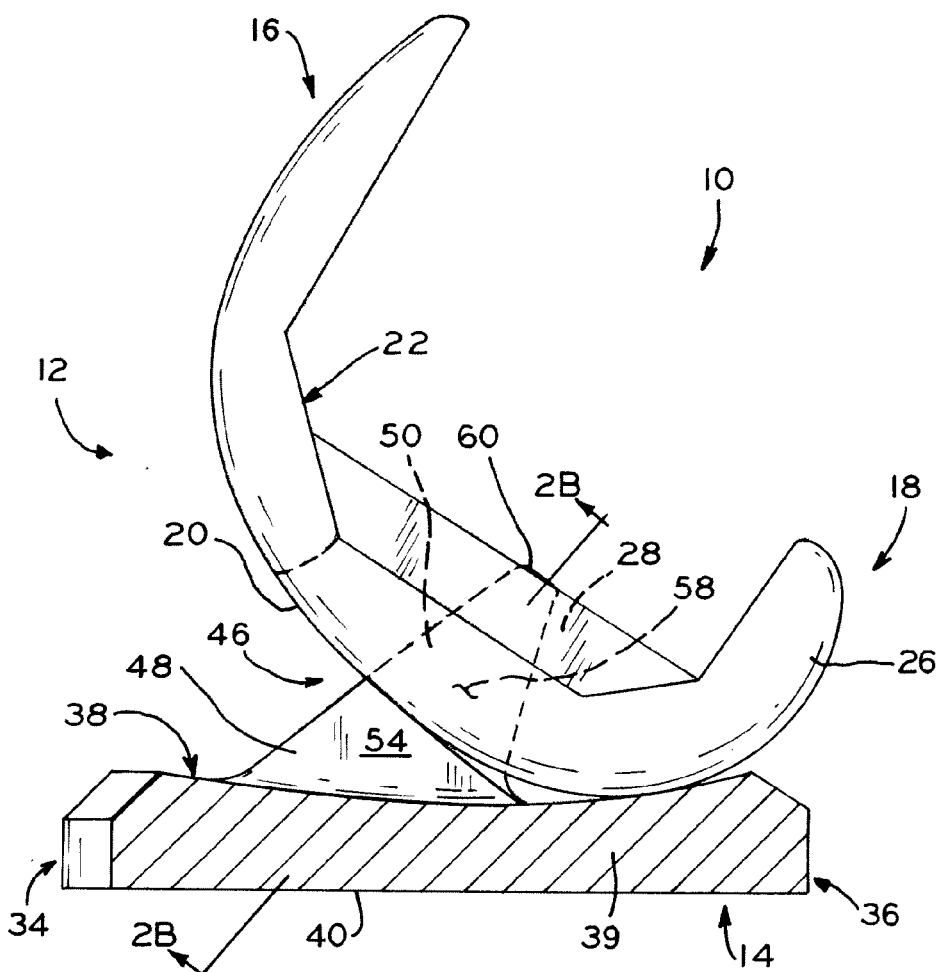
FIG. 2A is an elevation, partial section, side view of the knee joint prosthesis shown in FIG. 1A, shown in a flexion orientation.

As indicated above, the present disclosure provides a knee joint prosthesis which selectively allows or impedes internal/external rotation of the tibia depending on the level of flexion of the knee. More particularly, the knee joint prosthesis of the present disclosure reproduces the screw home mechanism of a natural knee by preventing internal/external rotation between full extension and a low level of flexion, i.e., less than about 10-20 degrees of flexion. The knee joint prosthesis permits internal/external rotation at higher levels of flexion. As the prosthesis is advanced from the low level of flexion to full extension, the femoral component cooperates with the tibial component to drive external rotation of the tibia. In order to prepare the tibia and femur for receipt of a knee joint prosthesis of the present disclosure, any known methods and apparatuses for preparation of the knee joint may be used.

Referring now to FIGS. 1A and 1B, knee joint prosthesis 10 includes femoral component 12 and tibial component 14. Femoral component 12 includes anterior end 16 and posterior end 18 (FIG. 1A), with a distal articulating surface 20 extending therebetween. A proximal fixation surface 22 is adapted for fixation to a resected distal femur using any known methods and apparatuses. Femoral component 12 includes lateral condyle 24 and medial condyle 26, as best shown in FIGS. 1B and 2B.

Figure 2B:
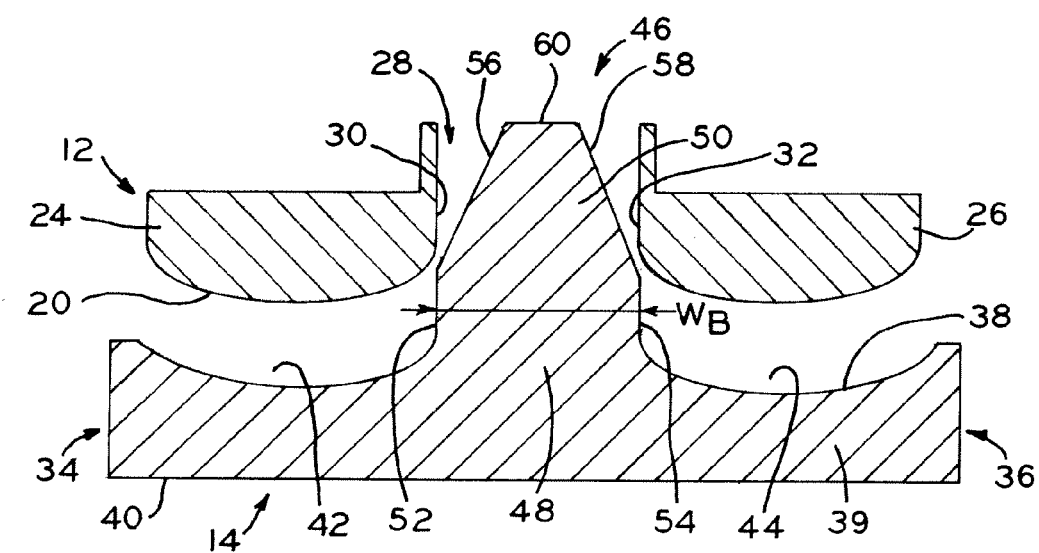
FIG. 2B is an elevation, section, end view of the knee joint prosthesis shown in FIG. 2A.

Referring to FIGS. 1B and 2B, intercondylar fossa 28 is disposed between the lateral condylar inner wall 30 of lateral condyle 24 and the medial condylar inner wall 32 of medial condyle 26. At least a portion of lateral condylar inner wall 30 and medial condylar inner wall 32 defines a substantially flat or planar sagittal surface, i.e., the planes defined by inner condylar walls 30, 32 are substantially parallel to a sagittal plane. Thus, intercondylar fossa 28 defines a channel between lateral and medial condyles 24, 26 of femoral component 12. As described in detail below, the channel-like nature of intercondylar fossa 28 cooperates with spine 46 formed in tibial component 14 to reproduce the screw-home mechanism of the natural knee.

Figure 3A:
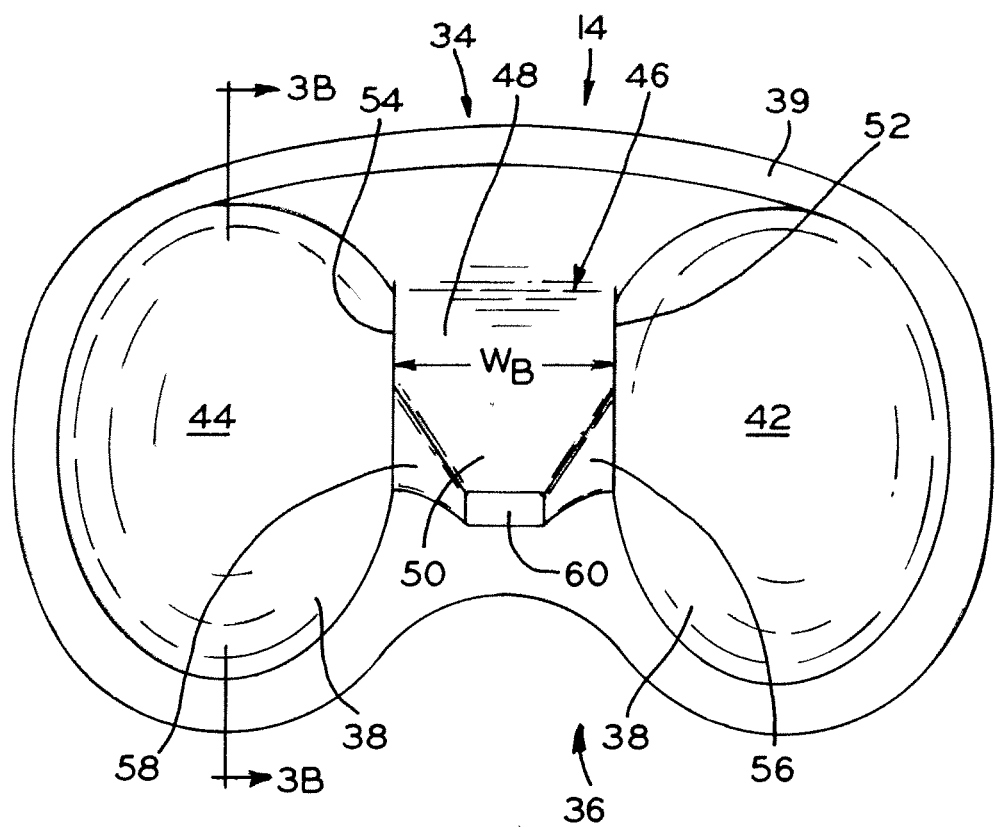
FIG. 3A is an plan view of the tibial component of the knee joint prosthesis shown in FIG. 1A.
Figure 3B:
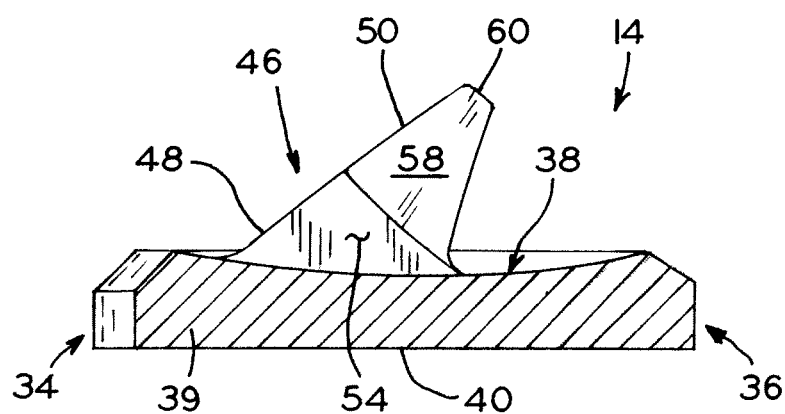
FIG. 3B is an elevation, section view of the tibial component shown in FIG. 3A.

As best seen in FIGS. 3A and 3B, tibial component 14 includes anterior end 34 and posterior end 36, with articulating surface 38 extending therebetween. Fixation surface 40 (FIG. 3B) is adapted to attach to a resected proximal tibia by any known methods and apparatuses. Tibial component 14 includes lateral compartment 42 and medial compartment 44, with lateral compartment 42 shaped and positioned to correspond with lateral condyle 24 of femoral component 12, and medial compartment 44 shaped and positioned to correspond with medial condyle 26 of femoral component 12. An intercondylar eminence, such as spine 46, is disposed between lateral and medial compartments 42, 44 and extends upwardly or proximally from articulating surface 38. Spine 46 cooperates with intercondylar fossa 28 of femoral component 12 (FIGS. 1B and 2B) to limit internal/external rotation of tibial component 14 at certain levels of flexion of knee joint prosthesis 10, and to permit internal/external rotation at other levels of flexion, as described below.

Referring to FIG. 2B, spine 46 includes base 48 and peak 50, with base 48 disposed between tibial component body 39 and peak 50. Base 48 defines lateral base wall 52 and medial base wall 54, each of which has a substantially flat or planar sagittal surface, i.e., at least a portion of base walls 52, 54 define planar surfaces which are substantially parallel with a sagittal plane. Peak 50 defines lateral peak surface 56 and medial peak surface 58 extending from the tops of lateral base wall 52 and medial base wall 54, respectively. Lateral and medial peak surfaces 56, 58 taper to a summit 60 disposed at the proximal terminus of peak 50. Although the illustrated embodiment shows peak 50 as the uppermost (i.e., most proximal) portion of spine 46, with summit 60 as the narrowest point of peak 50, it is within the scope of the present disclosure that peak 50 may also be disposed between base 48 and another structure, such that summit 60 may abut a further proximal structure forming a part of spine 46.

As best seen in FIG. 3B, medial base wall 54 is bounded by three edges to form a generally triangular shape, with an anterior side of the triangle coincident with the anterior face of peak 50 and two points of the triangle disposed on articular surface 38 of tibial component 14. As best seen in FIG. 3A, medial peak surface 58 and lateral peak surface 56 form trapezoidal shapes extending from the triangular shapes of medial base wall 54 and lateral base wall 52, respectively, at inflection points. As illustrated in FIGS. 1A-2B and discussed in more detail below, this "triangular" shape allows base walls 52, 54 of spine 46 to cooperate with inner condylar walls 30, 32 to selectively prevent or permit internal/external rotation of tibial component 14 with respect to femoral component 12 when knee joint prosthesis 10 toggled between extended and flexed orientations.

Referring now to FIGS. 2B and 3A, base 48 has width $W_B$ defined between lateral base wall 52 and medial base wall 54. Width $W_B$ corresponds with the width of intercondylar fossa 28. Lateral base wall 52 is abutting or closely adjacent lateral condylar inner wall 30, and medial base wall 54 is abutting or closely adjacent medial condylar inner wall 32 when tibial component 14 is in low-flexion or extension orientations relative to femoral component 12. On the other hand, the transverse distance between lateral peak surface 56 and medial peak surface 58 is less than width $W_B$, with such transverse distance transitioning from being nearly equal to width $W_B$ at the junction between peak 50 and base 48, to being substantially less than width $W_B$ proximate summit 60 of peak 50. This reduced transverse width of peak 50 cooperates with intercondylar fossa 28 to allow internal/external rotation of tibial component 14 relative to femoral component 12 at certain flexion orientations of knee joint prosthesis 10.

Width $W_B$ of base 48 of spine 46 may be as little as 15 mm, 16 mm or 17 mm, and as large as 20 mm, 23 mm, or 25 mm, or width $W_B$ may be within any range delimited by any of the foregoing values. Similarly, the taper of peak 50, i.e., the reduction in the transverse width of peak 50 between base 48 and summit 60 may result in a width of summit 60 that is as little as 10 mm, 12 mm or 14 mm, and as large as 16 mm, 18 mm, or 20 mm, or the width of summit 60 may be within any range delimited by any of the foregoing values.

The clearance between condylar inner walls 30, 32 of intercondylar fossa 28 and base 48 of spine 46 determines the extent of prevention of internal/external rotation in knee joint prosthesis 10, as described in detail below. This clearance may be as little as nearly zero mm, 0.03 mm or 0.06 mm, and as large as 0.10 mm, 0.15 mm, or 0.20 mm, or may be within any range delimited by any of the foregoing values.

Width $W_B$, the taper of peak 50 and the clearance between base 48 and intercondylar fossa 28 may be chosen based on various design considerations, such as the overall size of knee joint prosthesis 10, the desired clearance between spine 46 and corresponding structures on femoral component 12 (described below), and the like. For example, in one exemplary embodiment, width $W_B$ of base 48 may be about 18.1 mm wide, with a near-zero clearance with intercondylar fossa 28. In this embodiment, the transverse width of peak 50 may taper to about 15.0 mm at summit 60.

When knee joint prosthesis 10 is in an extension orientation, femoral component 12 is positioned upon tibial component 14 such that a leg with knee joint prosthesis 10 implanted in the leg would be fully extended. In this extension orientation, illustrated in FIGS. 1A and 1B, at least a portion of intercondylar fossa 28 is closely engaged with base 48. When so engaged, little or no gap exists between lateral condylar inner wall 30 of femoral component 12 and lateral base wall 52 of tibial component 14. Likewise, on the medial side of knee joint prosthesis 10, little or no gap exists between medial condylar inner wall 32 of femoral component 12 and medial base wall 54 of tibial component 14 in the extension orientation. As a result of the interaction between walls 30, 52 and walls 32, 54, tibial component 14 and femoral component 12 are not internally or externally rotatable relative to one another, i.e., tibial component is fixed or locked against internal/external rotation.

Further, the interaction between walls 30, 52 and walls 32, 54 in the extension orientation defines the orientation of components 12, 14 with respect to internal/external rotation. As will be described in more detail below, this "locked" rotational orientation occurs after tibial component 14 has been externally rotated in the final stages of flexion. This externally rotated orientation of tibial component 14 is similar to an anatomical knee which has externally rotated under the influence of the screw home mechanism as the knee is extended.

Referring from FIGS. 1A and 1B to FIGS. 2A and 2B, flexion of knee joint prosthesis 10 moves femoral component 12 relative to tibial component 14 to a flexed orientation. In this flexed orientation, lateral and medial condylar inner walls 30, 32 have moved posteriorly and proximally so that walls 30, 32 are no longer engaged with lateral and medial base walls 50, 54 of spine 46, respectively. Instead, condylar inner walls 30, 32 are proximate lateral and medial peak surfaces 56, 58, of peak 50 of spine 46. Because the transverse dimension of peak 50 is less than width $W_B$ of base 48, as discussed above, external or internal rotation of tibia 14 with respect to femoral component 12 becomes possible. Further, the gradual reduction of width of peak 50 from the interface between peak 50 and base 48 to summit 60 of peak 50 results in a gradual increase in the ability of tibial component 14 to internally or externally rotate with respect to femoral component 12. Thus, only a small amount of internal/external rotation will be possible just after intercondylar fossa 28 of femoral component 12 has disengaged base 48 of tibial component 14 (as shown in FIGS. 2A and 2B). As knee joint prosthesis 10 flexes further, however, intercondylar fossa 28 will engage the narrower proximal parts of peak 50, and more internal/external rotation will be permitted.

In the exemplary embodiment illustrated in FIGS. 1A-2B, intercondylar fossa 28 disengages from base 48 at between about 10 degrees to about 15 degrees of leg extension. However, it is within the scope of the present disclosure that this disengagement may occur at as little as 5 degrees, 10 degrees or 15 degrees and as much as 20 degrees, 25 degrees or 30 degrees of extension, or within any range defined by any of the foregoing values. Complete disengagement of intercondylar fossa 28 from spine 46 may or may not occur at a larger degree of flexion.

Referring from FIGS. 2A and 2B to FIGS. 1A and 1B, knee joint prosthesis may also be moved from a flexion orientation to an extension orientation. When so moved, intercondylar fossa 28 of femoral component 12 and spine 46 of tibial component 14 cooperate to urge external rotation of the tibia in certain stages of flexion. In later stages of flexion and in extension, the rotational orientation of the tibia becomes fixed in the externally rotated position, thereby replicating the screw home mechanism of an anatomic knee.

As tibial component 14 is articulated with femoral component 12 from a highly flexed orientation toward extension, lateral and/or medial peak surfaces 56, 58 of peak 50 cooperate with lateral and/or medial condylar inner walls 30, 32 to urge external rotation of tibial component 14 with respect to femoral component 12. This urging becomes more pronounced as the transverse width of peak 50 increases toward base 48 (as discussed above). Thus, as intercondylar fossa 28 articulates with peak 50 of spine 46 during extension, the tibia is smoothly externally rotated toward the external rotation orientation, and this externally rotated orientation is locked throughout the final 10-20 degrees of flexion and in extension. This urged external rotation mimics the screw home mechanism of an anatomic knee, and may occur over a range of flexion, such as from about 45 degrees of flexion to between 20 and 10 degrees of flexion.

Referring now to FIG. 2A, as knee joint prosthesis 10 approaches the low-flexion orientation, lateral and medial condylar inner walls 30, 32 begin to reengage lateral and medial base walls 52, 54, respectively. This engagement prevents interior/exterior rotation of tibial component 14 with respect to femoral component 12, thereby affecting the lock against further rotation. With intercondylar fossa 28 and base 48 cooperating to lock tibial component 14 in an externally rotated orientation, the tibia is placed in a high stability position that is consistent with the screw home mechanism of an anatomic knee.

It is within the scope of the present disclosure that the urged external rotation of tibial component 14 with respect to femoral component 12 may occur throughout any range of flexion, or may occur abruptly. For example, the peak portion of a tibial spine may feature an abrupt transition from the base to the peak, as opposed to the gradual transition from base 48 to peak 50. This abrupt transition may take the form of a "step" or abrupt change in width, and results in the urged external rotation of tibial component 14 occurring over a narrower range of flexion. Alternatively, the peak portion of the spine may be made taller so that it extends further proximally. This taller peak may include a gradually reducing transverse width, similar to peak 50 of spine 46. The taller peak will allow the urged external rotation of tibial component 14 to occur over a larger range of extension.

Referring generally to FIGS. 4A-5B, knee joint prosthesis 110 includes femoral component 112 and tibial component 114. Except where otherwise noted, reference numbers of knee joint prosthesis 110 correspond with reference numbers of knee joint prosthesis 10, with reference numbers of knee joint prosthesis 110 having 100 added thereto. Moreover, knee joint prosthesis 110 replicates the screw home mechanism of an anatomic knee, similar to knee joint prosthesis 10. However, intercondylar fossa 128 of femoral component 112 has varying widths corresponding to various degrees of flexion, while intercondylar eminence or spine 146 has a substantially constant width, as described below.

As best seen in FIGS. 6A and 6B, femoral component 112 includes anterior end 116 and posterior end 118 with articulating surface 120 extending therebetween. Fixation surface 122 disposed opposite articulating surface 120 is adapted for fixation of femoral component 112 to a distal resected femur. Referring to FIG. 6B, femoral component 112 includes lateral condyle 124 and medial condyle 126, with lateral condyle 124 defining lateral condylar inner wall 130 and medial condyle 126 defining medial condylar inner wall 132.

Figure 5A:
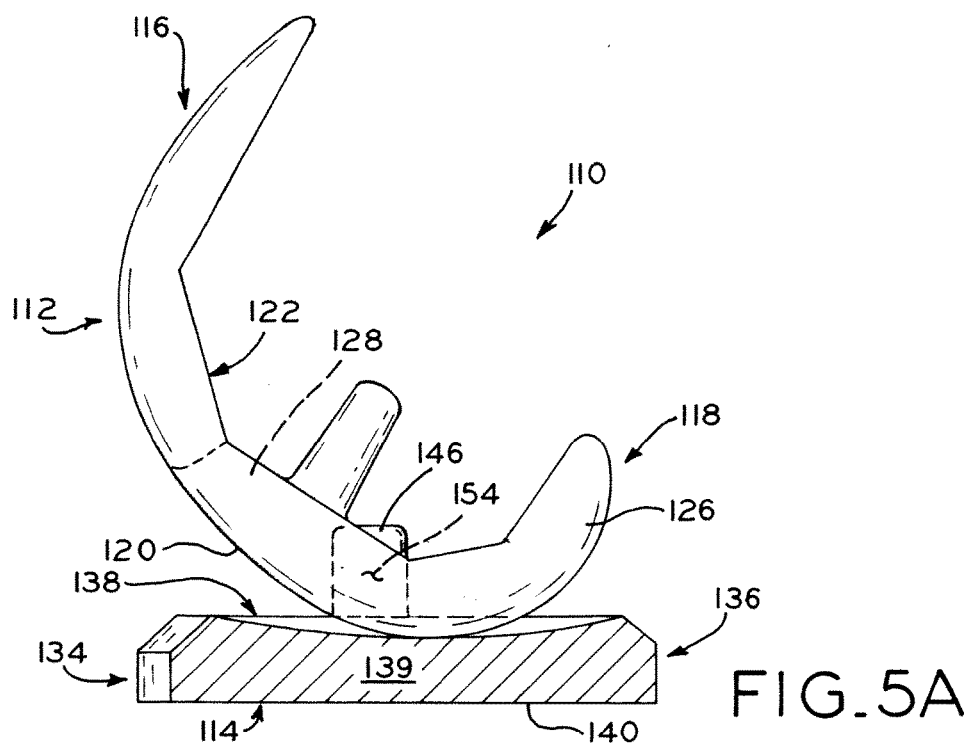
FIG. 5A is an elevation, section, end view of the knee joint prosthesis of FIG. 4A, shown in a flexion orientation.
Figure 5B:
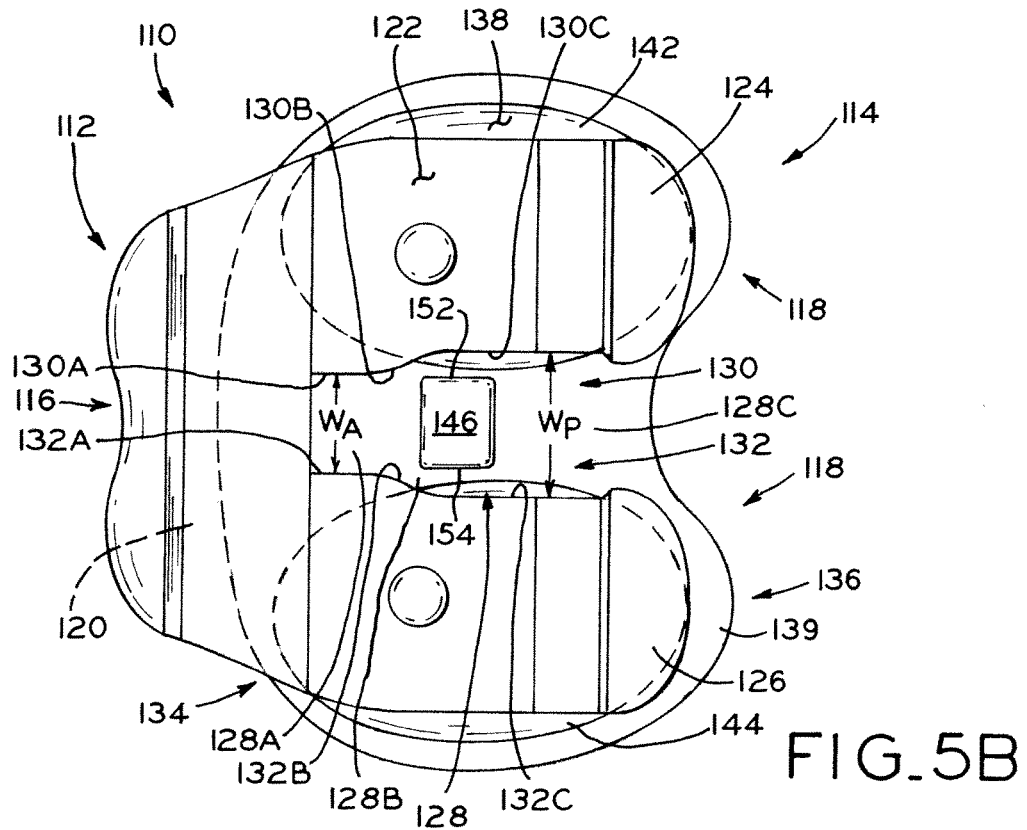
FIG. 5B is a plan view of the knee joint prosthesis of FIG. 5A.

As best seen in FIGS. 4B, 5B and 6B, femoral component 112 includes intercondylar fossa 128, which is formed by the space between lateral and medial condylar inner walls 130, 132. Lateral condylar inner wall 130 includes anterior lateral wall segment 130A and posterior lateral wall segment 130C, with transition wall segment 130B extending therebetween. Medial condylar inner wall 132 includes anterior medial wall segment 132A, posterior medial wall segment 132C and transitional medial wall segment 132B extending therebetween. Intercondylar fossa 128 includes anterior space 128A disposed between anterior lateral and medial wall segments 130A, 132A and defining width $W_A$ (FIGS. 5B and 6B), posterior space 128C disposed between posterior lateral and medial wall segments 130C, 132C and defining width $W_P$ (FIGS. 5B and 6B). Transitional space 128B of intercondylar fossa 128 is disposed between transitional lateral and medial wall segments 130B, 132B and between anterior space 128A and posterior space 128C. As described in detail below, anterior transitional and posterior spaces 128A, 128B, 128C cooperate with tibial component 114 to permit or prevent interior/exterior rotation of tibial component 114 with respect to femoral component 112, depending on the flexion orientation of knee joint prosthesis 110.

Referring now to FIGS. 4A-5B, tibial component 114 defines tibial component body 139 having anterior end 134 and posterior end 136, with articulating surface 138 extending therebetween. A fixation surface 140 (FIGS. 4A and 5A) is disposed opposite articulating surface 138, and is adapted to attach to a resected proximal tibia by any known methods and apparatuses. Articulating surface 138 includes lateral compartment 142 and medial compartment 144, with intercondylar eminence or spine 146 disposed therebetween and extending upwardly or proximally from articulating surface 138. Spine 146 includes lateral spine wall 152 and medial spine wall 154, with spine walls 152, 154 disposed mutually opposite one another in a generally parallel configuration. Spine walls 152, 154 are shown as having a generally planar configuration, but may also be rounded.

Referring now to FIGS. 4A and 4B, knee joint prosthesis 110 is shown in an extension orientation in which anterior lateral wall segment 130A abuts or is closely adjacent lateral spine wall 152, and anterior medial wall segment 132A abuts or is closely adjacent medial spine wall 154. Therefore, anterior space 128a of intercondylar fossa 128 captures spine 146, thereby preventing internal/external rotation of tibial component 114 with respect to femoral component 112.

Referring now to FIGS. 5A and 5B, when knee joint prosthesis 110 moves from extension to low flexion, such as about 10 to 20 degrees of flexion, spine 146 moves out of anterior space 128A of intercondylar fossa 128 and into transitional space 128B. Therefore, lateral spine wall 152 is proximate transitional lateral wall segment 130B, and medial spine wall 154 is proximate transitional medial wall segment 132B. Some internal/external rotation of tibial component 114 with respect to femoral component 112 will now be permitted.

As knee joint prosthesis 110 is flexed further, such as to up to about 45 degrees, spine 146 exits transitional space 128B and enters posterior space 128C of intercondylar fossa 128. In this orientation, lateral spine wall 152 is proximate posterior lateral wall segment 130C and medial spine wall 154 is proximate posterior wall segment 132C, and constraint on internal/external rotation of tibial component 114 with respect to femoral component 112 is further relaxed.

When knee joint prosthesis 110 is articulated from a flexed orientation back to an extension orientation, spine 146 moves from posterior space 128C into transitional space 128B and eventually into anterior space 128A of intercondylar fossa 128. Similar to the gradually changing width of peak 50 of spine 46 (discussed above), the gradual reduction from width $W_P$ of posterior space 128C to the smaller width $W_A$ of anterior space 128A and transitional space 128B helps guide spine 146 into the locked position corresponding with an extension or low-flexion orientation of knee joint prosthesis 110. Further, this gradual transition occurring in transitional space 128B urges tibial component 114 to externally rotate, so that tibial component is in an externally rotated extended position when locked against further rotation. As discussed above, this locked, externally rotated position promotes stability of knee joint prosthesis 110. Moreover, knee joint prosthesis 110 mimics or reproduces the screw home mechanism of an anatomic knee joint.

Widths $W_A$, may cooperate with the width of spine 146 to provide varying levels of clearance between spine 146 and intercondylar fossa 128, as described above with respect to knee joint prosthesis 10. Moreover, in certain embodiments, the width of spine 146 may generally correspond with width $W_B$ of base 48 of spine 46, while the difference between widths $W_A$ and $W_P$ of intercondylar fossa 128 may generally correspond with the difference between difference between width $W_B$ of base 48 and the width of summit 60 resulting from the tapering of spine 46.

Advantageously, knee joint prostheses 10, 110 promote stability of a knee joint by preventing the potentially destabilizing influence of internal or external rotation during the last stages of knee extension, i.e., the last 10 to 15 degrees of extension. Prior to the terminal extension phase, external rotation of the tibia is urged by knee joint prosthesis 10, 110 to orient the tibia in a highly stabile position, and to lock the tibia against internal/external rotation in that position. This urged external rotation and subsequent locking action is similar to the screw home mechanism of an anatomic knee, and therefore facilitates behavior of knee joint prostheses 10, 110 that more closely approximates a healthy anatomic knee joint.

The illustrated embodiments herein illustrate knee prostheses 10, 110 adapted for use in a right knee. However, the principles of the present disclosure are also applicable to applications in a left knee.

While this invention has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this invention pertains and which falls within the limits of the appended claims.

What is claimed is:

1. A knee joint prosthesis moveable between an extension orientation and a flexion orientation, the prosthesis comprising:
    a femoral component comprising:
        a lateral condyle having a lateral condylar inner wall;
        a medial condyle having a medial condylar inner wall; and
        an intercondylar fossa bounded on two sides by said lateral condylar inner wall and said medial condylar inner wall; and
    a tibial component comprising:
        a tibial articulating surface;
        a spine extending proximally from said tibial articulating surface at a first junction, said spine including a base adjacent said tibial articulating surface, said base having a lateral base wall and an opposed medial base wall with a base width defined between said lateral base wall and medial base wall, each of said lateral base wall and said medial base wall is parallel to a sagittal plane, said spine including a peak disposed proximally of said base and having a lateral peak surface and an opposed medial peak surface, a peak width defined between said lateral peak surface and medial peak surface, said peak width less than said base width;
    said lateral condylar inner wall engaging with said lateral base wall and said medial condylar inner wall engaging with said medial base wall, to prevent internal rotation and external rotation of said tibial component when the knee joint prosthesis is in the extension orientation; and
    said lateral condylar inner wall cooperating with said lateral peak surface and said medial condylar inner wall cooperating with said medial peak surface, to permit at least one of internal rotation and external rotation of said tibial component when the knee joint prosthesis is in the flexion orientation.

2. The knee joint prosthesis of claim 1, wherein said peak width tapers from equal to said base width at said first junction and a second junction between said peak and said base approximately midway along the spine to substantially less than said base width at a proximal summit of said peak, said second junction between said peak and said base defining an inflection point along said spine.

3. The knee joint prosthesis of claim 2, wherein said spine of said tibial component remains engaged with said intercondylar fossa over a range from said first junction to said inflection point and disengages said intercondylar fossa of said femoral component over a range from said inflection point to said summit, said inflection point being located at an orientation of the knee prosthesis corresponding to about 10 degrees to about 45 degrees flexion.

4. The knee joint prosthesis of claim 1, wherein the flexion orientation of the knee prosthesis corresponds to an orientation of at least 20 degrees flexion.

5. The knee joint prosthesis of claim 1, wherein the flexion orientation of the knee prosthesis corresponds to an orientation of at least 15 degrees flexion.

6. The knee joint prosthesis of claim 1, wherein the flexion orientation of the knee prosthesis corresponds to an orientation of at least 10 degrees flexion.

7. The knee joint prosthesis of claim 1, wherein said peak and said base extend along approximately equal lengths of an anterior surface of said spine.

8. The knee joint prosthesis of claim 1, wherein said spine is stepped between said base and said peak.

9. The knee joint prosthesis of claim 1 wherein said peak is tapered, and wherein said tapered peak produces a screw-home mechanism of the femoral component in the range of about forty-five degrees to about twenty degrees of flexion and said base locks said femoral component from rotation from about twenty degrees of flexion to zero degrees of flexion.

10. A knee joint prosthesis moveable between an extension orientation and a flexion orientation, the prosthesis comprising:
    a femoral component comprising:
        a lateral condyle having a lateral condylar inner wall;
        a medial condyle having a medial condylar inner wall; and
        an intercondylar fossa bounded on two sides by said lateral condylar inner wall and said medial condylar inner wall; and
    a tibial component comprising:
        a tibial articulating surface; and
        a spine extending proximally from said tibial articulating surface, said spine including a lateral spine wall and an opposed medial spine wall, each of said lateral spine wall and said medial spine wall is parallel to a sagittal plane at a base, said lateral spine wall and said medial spine wall tapering to a summit at a peak so that portions of said lateral and medial spine walls defining said peak are disposed at a different angle relative to said sagittal plane than portions of said lateral and medial spine walls defining said base;
    said lateral condylar inner wall engaging with said lateral spine wall and said medial condylar inner wall engaging with said medial spine wall, to prevent internal rotation and external rotation of said tibial component when the knee joint prosthesis is in the extension orientation and the femoral component engages the base of the spine, and to permit at least one of internal rotation and external rotation of said tibial component when the knee joint prosthesis is in the flexion orientation by disengaging from the base to cooperate with the peak at an orientation of the knee prosthesis corresponding to less than about 45 degrees of flexion.

11. The knee joint prosthesis of claim 10, wherein the flexion orientation of the knee prosthesis corresponds to an orientation of at least 20 degrees flexion.

12. The knee joint prosthesis of claim 10, wherein the flexion orientation of the knee prosthesis corresponds to an orientation of at least 15 degrees flexion.

13. The knee joint prosthesis of claim 10, wherein the flexion orientation of the knee prosthesis corresponds to an orientation of at least 10 degrees flexion.

14. The knee joint prosthesis of claim 10, wherein said lateral and medial spine walls first disengage from said lateral and medial condylar inner walls, respectively, as the knee joint prosthesis transitions from the extension orientation to the flexion orientation at about 10 degrees to about 45 degrees flexion.

15. The knee joint prosthesis of claim 10, wherein said peak having a peak width less than a width between said lateral and medial spine walls such that said peak permits internal/external rotation of said tibial component when the knee joint prosthesis is in the flexion orientation.

* * * * *